(12) United States Patent
Zeile

(10) Patent No.: US 8,263,933 B2
(45) Date of Patent: Sep. 11, 2012

(54) DEVICE AND METHOD FOR ANALYZING AN ORGANIC SAMPLE

(75) Inventor: Ulrike Zeile, Heidenheim (DE)

(73) Assignee: Carl Zeiss NTS GmbH, Oberkochen (DE)

( * ) Notice: Subject to any disclaimer, the term of this patent is extended or adjusted under 35 U.S.C. 154(b) by 496 days.

(21) Appl. No.: 12/584,284

(22) Filed: Sep. 2, 2009

(65) Prior Publication Data

US 2010/0074474 A1 Mar. 25, 2010

(30) Foreign Application Priority Data

Sep. 4, 2008 (DE) .................. 10 2008 041 813

(51) Int. Cl.
*H01J 49/26* (2006.01)
*H01J 37/00* (2006.01)
*B01D 59/44* (2006.01)

(52) U.S. Cl. .................. 250/306; 250/307; 250/423 R; 250/424; 250/281; 250/282

(58) Field of Classification Search .................. 250/306, 250/307, 281, 282, 423 R, 424
See application file for complete search history.

(56) References Cited

U.S. PATENT DOCUMENTS

| | | | |
|---|---|---|---|
| 4,835,383 A * | 5/1989 | Mahoney et al. ............. 250/281 | |
| 5,035,787 A | 7/1991 | Parker et al. | |
| 5,270,552 A | 12/1993 | Ohnishi et al. | |
| 5,504,340 A | 4/1996 | Mizumura et al. | |
| 5,583,344 A | 12/1996 | Mizumura et al. | |
| 6,410,926 B1 | 6/2002 | Munro et al. | |
| 7,095,021 B2 * | 8/2006 | Shichi et al. .................. 250/307 |
| 8,093,556 B2 * | 1/2012 | Zeile ............................ 250/306 |
| 2002/0125423 A1 | 9/2002 | Ebeling et al. | |
| 2003/0209667 A1 | 11/2003 | Petrov et al. | |
| 2006/0022150 A1 | 2/2006 | Takeuchi et al. | |
| 2006/0097197 A1 | 5/2006 | Sakaguchi | |
| 2006/0118711 A1 | 6/2006 | Murayama et al. | |
| 2007/0138385 A1 | 6/2007 | Kulp et al. | |
| 2010/0155591 A1 | 6/2010 | Matsuo | |

FOREIGN PATENT DOCUMENTS

| | | |
|---|---|---|
| DE | 10 2005 012 8 | 9/2006 |
| DE | 10 2005 012 824 A1 | 9/2006 |
| EP | 0 453 808 A1 | 10/1991 |
| EP | 1 956 634 A1 | 8/2008 |
| EP | 2 037 260 A1 | 3/2009 |
| GB | 2 386 747 A | 9/2003 |
| GB | 2 414 594 A | 11/2005 |
| JP | 2005121413 A1 | 5/2005 |
| SU | 1205208 A | 1/1986 |
| WO | WO88/09049 | 11/1988 |
| WO | WO03/027682 A2 | 4/2003 |
| WO | WO2005/001869 A2 | 1/2005 |
| WO | WO2006/026569 A2 | 3/2006 |
| WO | WO 2006/097321 A1 | 3/2006 |
| WO | WO 2007/145232 A1 | 12/2007 |

\* cited by examiner

*Primary Examiner* — Nikita Wells

(74) *Attorney, Agent, or Firm* — Muirhead and Saturnelli, LLC

(57) ABSTRACT

A device and method for analyzing an organic sample provide high spatial resolution. A focused ion beam is directed onto the organic sample. Fragments detached from the sample are examined using mass spectroscopy.

19 Claims, 6 Drawing Sheets

DEVICE AND METHOD FOR ANALYZING AN ORGANIC SAMPLE

TECHNICAL FIELD

This application relates to a device and method for analyzing an organic sample (hereinafter also referred to as organic substance) that results in high spatial resolution.

BACKGROUND OF THE INVENTION

The use of an ion beam column for repairing semiconductor masks is known from the prior art. The ion beam column has an ion source, which provides a plurality of ions of different suitable elements, which have different ion masses. The ions are combined in an ion beam and directed toward a semiconductor mask to be repaired. A desired type of ions is selected on the basis of their mass and their charge with the help of a filter which provides both an electric field and a magnetic field. Ultimately only these selected ions are focused onto the semiconductor mask as an ion beam. Due to an interaction of the ion beam incident on the semiconductor mask with the material of the semiconductor mask, interaction particles are generated, in particular secondary electrons or secondary ions, which are emitted from the semiconductor mask. A detector detects the interaction particles. Reference is made to U.S. Pat. No. 5,035,787 and WO 88/09049 regarding the above prior art, which are incorporated herein by reference.

As mentioned previously, the known method relates to the repair of semiconductor masks only, however, not to an analysis of an organic sample, for example, of a cell structure.

The method of matrix assisted laser desorption/ionization, known by its abbreviation MALDI, is used, in particular for analyzing an organic sample. This is a method for ionizing molecules. MALDI is based on co-crystallization of a matrix to be examined with an analyte. Excitation with the aid of laser pulses causes fragments on the surface of a crystal to detach. These fragments are examined using mass spectrometry. The mass spectra generated thereby are compared with other mass spectra which are stored in a database. Each mass spectrum of the other mass spectra reproduces properties of a well-defined material or substance, so that by comparing the generated mass spectra with the stored other mass spectra, conclusions may be drawn about the material or materials of the examined organic sample. However, MALDI provides a spatial resolution of usually only 0.1 mm, at best of 25 µm. This resolution is insufficient for many applications.

However, secondary ion mass spectrometry, also known by its abbreviation SIMS, is known as a high spatial resolution method. In this method, the surface of a sample to be examined is irradiated with a focused primary ion beam. The secondary ions obtained here, emitted by the surface of the sample, are detected and examined using mass spectrometry. The secondary ions are selected and identified on the basis of their ion mass, so that conclusions may be drawn about the sample. However, SIMS is barely or not at all used in analyzing organic substances in conjunction with a highly energy-rich primary ion beam incident on the organic substance. The reason therefor is that the primary ion beam often destroys the organic molecules of the organic substance in such a way that the organic molecules may no longer by distinguished by SIMS.

Accordingly, it would be desirable to provide a device and method for analyzing an organic sample that provides high spatial resolution.

SUMMARY OF THE INVENTION

According to the system described herein, a method for analyzing an organic sample includes initially generating ions which have a predefinable mass and/or a predefinable number of elementary charges. These ions may be bundled to form at least one ion beam and directed to at least one organic sample to be analyzed. Subsequently at least one fragment detached from the organic sample with the aid of the ion beam may be detected. An ion mass analyzer which generates a mass spectrum for the fragment may be used for this purpose. The ion mass analyzer may use the SIMS method, for example, which has been discussed previously. The mass spectrum thus generated may then be compared with at least one mass spectrum stored in a database, the stored mass spectrum having been obtained by analyzing a certain material prior to carrying out the method according to the system described herein. By comparing the generated mass spectrum with the stored mass spectrum, indications may thus be obtained regarding the material of which the organic sample is composed. In a next method step, the material of which the organic sample is composed may then be determined on the basis of the comparison between the generated mass spectrum and the stored mass spectrum.

The system described herein is based on the consideration that ions of a certain predefinable mass and/or a predefinable number of elementary charges contribute to relatively large fragments being detachable from an organic sample. These ions induce an organic sample to vibrate, so that relatively large fragments are detached from the organic sample. Large fragments may be easier to analyze compared to relatively small fragments. It is thus possible to draw conclusions about the material, for example, the material composition of an organic sample. The system described herein is also based on the consideration that an interaction zone of the ion beam on the organic sample may be sufficiently small that a high local resolution may be achieved.

The method according to the system described herein may be used in many applications in which an organic sample is to be analyzed. For example, it is provided to use the method according to the system described herein for analyzing transport processes in cells. The method according to the system described herein may also be used for examinations in which it is determined where exactly in a certain cell a certain substance (for example, a special active ingredient) is located. Furthermore, the method according to the system described herein may be used in an analysis of interactions between different crystallites in a pharmaceutical product. Another possible application is, for example, the analysis of penetration of dyes into paper and textiles. It should be specifically pointed out that the method according to the system described herein is not limited to the above-mentioned applications. Rather, the method according to the system described herein may be used in any application in which an organic sample is to be analyzed.

According to an embodiment of the method according to the system described herein, multiple fragments detached from the organic sample with the aid of the ion beam may be examined using mass spectrometry. Thus, different fragments from molecules are differentiated by mass and charge in the ion mass analyzer and represented in a mass spectrum, which may then be compared with one or more mass spectra stored in the database.

According to another embodiment of the method according to the system described herein, multiple mass spectra may be stored in the database, each of the multiple mass spectra originating from a different material. It m thus possible to simply and easily determine the composition of an organic sample. The mass spectra stored in the database may be obtained by methods different from the method according to the system described herein, for example, using MALDI. Alternatively or additionally, it is provided that the mass spectra stored in the database may be generated using the method according to the system described herein.

In another embodiment of the method according to the system described herein, both first ions and second ions may be generated when ions are generated. The first ions and the second ions may be ionized atoms or ionized molecules. The first ions may have a first predefinable mass and/or a first predefinable number of elementary charges. In contrast, the second ions may have a second predefinable mass and/or a second predefinable number of elementary charges. The second predefinable mass may be different from the first predefinable mass. Alternatively or additionally, it is provided that the second predefinable number of elementary charges may be different from the first predefinable number of elementary charges. The first ions may thus be different from the second ions. The first ions or the second ions may be selected from the generated ion beam and directed to the organic sample. In other words, a variety of ions of different masses and/or numbers of elementary charges may be generated in this embodiment. Using a selection process, ions of a well-defined mass and/or a well-defined number of elementary charges may be selected and focused onto the organic sample to be examined. A filter which provides both an electric field and a magnetic field (Wien filter) may be used, for example, for selecting the first ions or the second ions.

In another embodiment of the method according to the system described herein, it is provided that the first ions and/or the second ions may be or may contain at least one of the following elements: silicon (Si), chromium (Cr), iron (Fe), cobalt (Co), nickel (Ni), germanium (Ge), indium (In), tin (Sn), gold (Au), silver (Ag), lead (Pb), bismuth (Bi), neodymium (Nd), cesium (Cs), and arsenic (As). The ions may be ionized atoms or ionized molecules (for example, $AuSi^+$ or $AuSi^{2+}$). In an embodiment, it is provided that a variety of ions (ionized atoms or ionized molecules) of different elements may be generated, for example, of at least two or at least three of the above-mentioned elements. A "mixture" of different ions may thus be generated, which are then selected on the basis of their ion mass as explained above.

Alternatively or additionally, it is provided that the first ions and/or the second ions may contain a type of ions whose mass is greater than the mass of gallium. The use of gallium may be disadvantageous in some applications. Due to its relatively small mass, gallium has the characteristic of penetrating deep into an organic sample. In the case of some organic samples, this may result in the samples being damaged due to the deep penetration of gallium. Therefore, in these applications it is advantageous to select a type of ion whose mass is greater than the mass of gallium.

Furthermore, in another embodiment, it is provided that the first ions and/or the second ions may have a mass greater than 100 atomic mass units. Considerations have led to the conclusion that heavy ions are particularly well-suited for detaching fragments from an organic sample.

In a further embodiment of the method according to the system described herein, it is provided that the first ions and/or the second ions may be deposited on the organic sample. This is advantageous because some ion types reduce the work function of the organic sample needed for detaching a fragment and for its exit from the organic sample. Considerations have led to the conclusion that ions of gold or silver may be suitable for this purpose.

In a further embodiment of the method according to the system described herein, an organic sample may initially be immunolabeled. In this case, a specific organic molecule marked using a gold, platinum, or silver cluster may be introduced into the sample. The specific organic molecule may then be combined (together with the above-mentioned marker) with other organic molecules on the basis of the "key-lock principle." In an examination with the aid of an electron beam or a light beam, a very strong signal may be obtained at the locations where the specific organic molecules are located due to high backscatter or fluorescence. It is thus possible not only to draw conclusions about the composition of the organic sample, but also to draw conclusions about the behavior of the other organic molecules, for example, their distribution and bonding behavior.

The system described herein is not limited to the above-described marking method. Rather, any suitable marking method may be used. For example, in an embodiment of the method according to the system described herein, it is provided that different isotopes or different individual atoms are introduced into the organic sample as markers. The isotopes or individual atoms are recognizable with the aid of SIMS in such a way that conclusions about the organic sample may be drawn.

In a further embodiment of the method according to the system described herein, the ion beam may be focused onto the organic sample. This takes place, for example, in a suitable ion beam column. This makes it possible to perform an analysis of the composition of the organic sample at well-defined locations.

In a further embodiment, it is also provided that the method according to the system described herein may be carried out multiple times consecutively in order to thus obtain different data sets of the organic sample. In this way, two-dimensional or three-dimensional information about the organic sample may be compiled. For compiling two-dimensional information, the method may be carried out initially in one plane of the organic sample at least a first location of the organic sample. Information about the first location and the material determined at the first location may be stored as a first data set. Furthermore, the method may be carried out at least one second location of the organic sample. Information about the second location and the material determined at the second location may be stored as a second data set. For compiling three-dimensional information, the above-described method may be carried out not only with respect to one plane of the organic sample, but with respect to multiple planes which are situated one on top of the other or next to one another, for example. This is discussed again in greater detail elsewhere herein. Using this method it is possible, for example, to produce a false color image as a function of the material distribution of the organic sample.

In another embodiment of the method according to the system described herein, an image of the organic sample may be generated with the aid of a focused electron beam. For this purpose, it is provided in particular to scan the focused electron beam over the organic sample and to analyze the interaction particles generated to produce an image of the organic sample. Accordingly, it is possible to initially select a region of the organic sample with the aid of the image, this region being subsequently analyzed in greater detail with the aid of the method according to the system described herein. In another embodiment, it is provided that, while generating an image with the aid of the focused electron beam, mass spectra may be simultaneously generated and compared as described above. In yet another embodiment of the system described herein, it is provided to generate an image of the organic sample with the aid of the ion beam.

In a further embodiment of the method according to the system described herein, at least one dimension of a recess produced in the organic sample with the aid of the ion beam may be determined with the help of the image. This embodiment is based on the following considerations: in some applications, to examine an organic sample, it is initially cut at well-defined locations using the ion beam, so that recesses are formed. Alternatively, it is provided that a hole may be drilled in the organic sample with the aid of the ion beam. The material composition of the organic sample at the recess or hole may then be examined with the aid of the method according to the system described herein. The dimension of the recess (i.e., its depth) should be accurately determined so that conclusions may be drawn about the distribution of material in the organic sample. It is then possible to produce a material section image of the organic sample. It is furthermore possible to obtain three-dimensional information by examining, with the aid of the method according to the system described herein, different planes situated substantially perpendicularly to the recess and being gradually exposed using the ion beam.

Alternatively to the above-mentioned method, the dimension of the recess may also be determined via calculation if the rate of removal of material from the organic sample by the ion beam is known.

In a further embodiment, the method according to the system described herein may be combined with another examination method, namely energy-dispersive X-ray spectroscopy (also known by the abbreviation EDX). For this purpose, the above-mentioned focused electron beam may be used, which excites the atoms of the organic sample, so that X-ray radiation is emitted.

According further to the system described herein, a ion beam device is provided for carrying out the method having one of the above-mentioned features or a combination of multiple above-mentioned features. The ion beam device may have at least one ion generator that generates ions which have a predefinable mass and/or a predefinable number of elementary charges. Furthermore, at least one ion beam generator is provided for generating at least one ion beam from the generated ions. The ion beam device according to the system described herein may also have at least one ion beam director that directs the ion beam onto at least one organic sample. Furthermore, at least one detector may be provided that detects at least one fragment which is detached from the organic sample with the aid of the ion beam. The detector may include at least one ion mass analyzer that generates a mass spectrum. The mass spectrum may be generated with the aid of SIMS. In addition, the ion beam device according to the system described herein may have at least one comparing device that compares the generated mass spectrum with at least one mass spectrum stored in a database. Furthermore, at least one determining device may be provided that determines at least one material of which the organic sample is composed, the determination being based on the comparison of the generated mass spectrum with the stored mass spectrum.

In an embodiment of the ion beam device, an electron beam director may be provided which directs an electron beam onto the organic sample. It is provided in particular that the ion beam device may be provided with both an ion beam column and an electron beam column.

BRIEF DESCRIPTION OF THE DRAWINGS

Embodiments of the system described herein are explained below in greater detail using the figures, which are briefly described as follows.

DETAILED DESCRIPTION OF VARIOUS EMBODIMENTS

Figure 1:
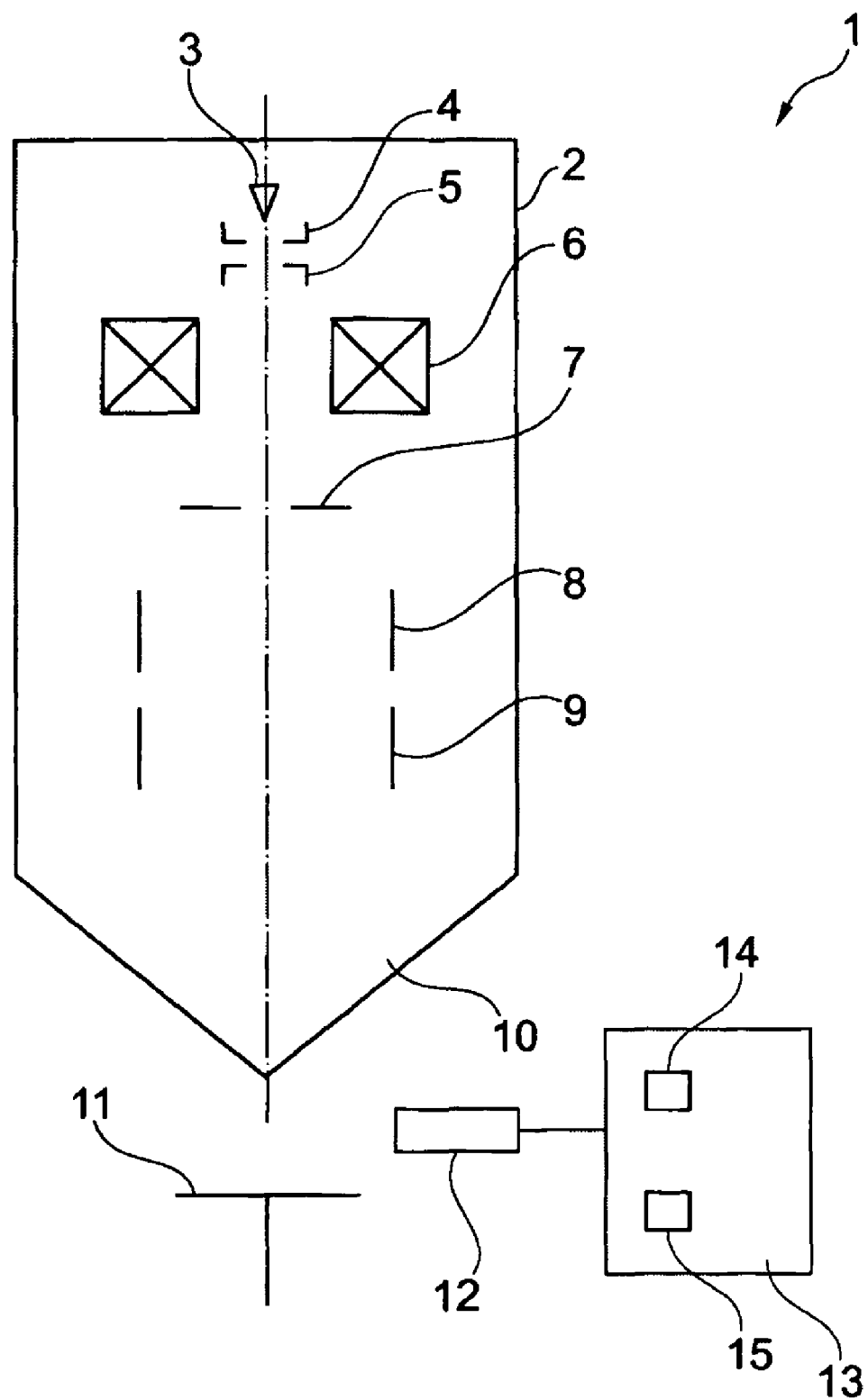
FIG. 1 shows a schematic view of an ion beam device according to an embodiment of the system described herein.

FIG. 1 shows a schematic representation of an ion beam device 1 using which the method according to the system described herein is carried out. The ion beam device 1 has an ion beam column 2 in which numerous units of the ion beam device 1 are situated. In particular, an ion source 3 is situated in the ion beam column 2. The ion source 3 generates ions which form an ion beam in the ion beam column 2. The ion source 3 may generate a variety of ions of different masses and/or numbers of elementary charges. Alternatively, it is provided that only one single ion type may be made available by the ion source 3. In the embodiment illustrated in FIG. 1, it is provided, for example, that the variety of ions may have or contain ions of a plurality of the following elements: silicon (Si), chromium (Cr), iron (Fe), cobalt (Co), nickel (Ni), germanium (Ge), indium (In), tin (Sn), gold (Au), silver (Ag), lead (Pb), bismuth (Bi), neodymium (Nd), cesium (Cs), and arsenic (As). The ions may be ionized atoms or ionized molecules (for example, $AuSi^+$ or $AuSi^{2+}$). It is also provided, for example, that the variety of ions (ionized atoms or ionized molecules) may contain ion types whose mass is greater than the mass of gallium. Furthermore, it is provided that the variety of ions may have ions whose mass is greater than 100 atomic mass units, as explained above.

The variety of ions may be accelerated to a predefinable potential with the aid of an electrode 4 and then passed through a condenser lens 5. A Wien filter 6 may be situated downstream from the condenser lens 5. The Wien filter 6 may provide both an electric field and a magnetic field in such a way that ions having a well-defined mass and/or a well-defined number of elementary charges may be selected from the variety of ions that form the ion beam. Only these selected ions remain in the ion beam and are then directed toward an organic sample 11 to be examined. The non-selected ions may thus be extracted from the ion beam.

The ion beam formed by the selected ions is passed through an aperture 7 and then reaches a deflector system, which is composed of electrostatic and/or magnetic deflector units. The deflector system may have any suitable design. In the embodiment shown here, a first electrode system 8 and a second electrode system 9 are provided, which may be scanning electrodes. The ion beam formed by the selected ions may be scanned over the organic sample 11 with the aid of the first electrode system 8 and the second electrode system 9. The ion beam may be focused onto the organic sample 11 with the aid of an objective lens 10.

When the ion beam hits the surface of the organic sample 11, fragments are detached from the organic sample 11. The detachment is produced by vibration excitations of the organic sample 11, induced by the ion beam hitting the surface of the organic sample 11. The fragments are now examined using mass spectrometry. An ion mass analyzer 12 may be provided for this purpose, which generates a mass spectrum of the fragments with the aid of SIMS. The generated mass spectrum may then be compared with a plurality of mass spectra which are stored in a memory unit 14 of a control unit 13. The generated mass spectrum may be compared with the stored mass spectra with the aid of a processor 15 of the control unit 13. In this way, it is possible to determine the material of which the organic sample 11 or the fragment of the organic sample 11 is composed.

Figure 2:
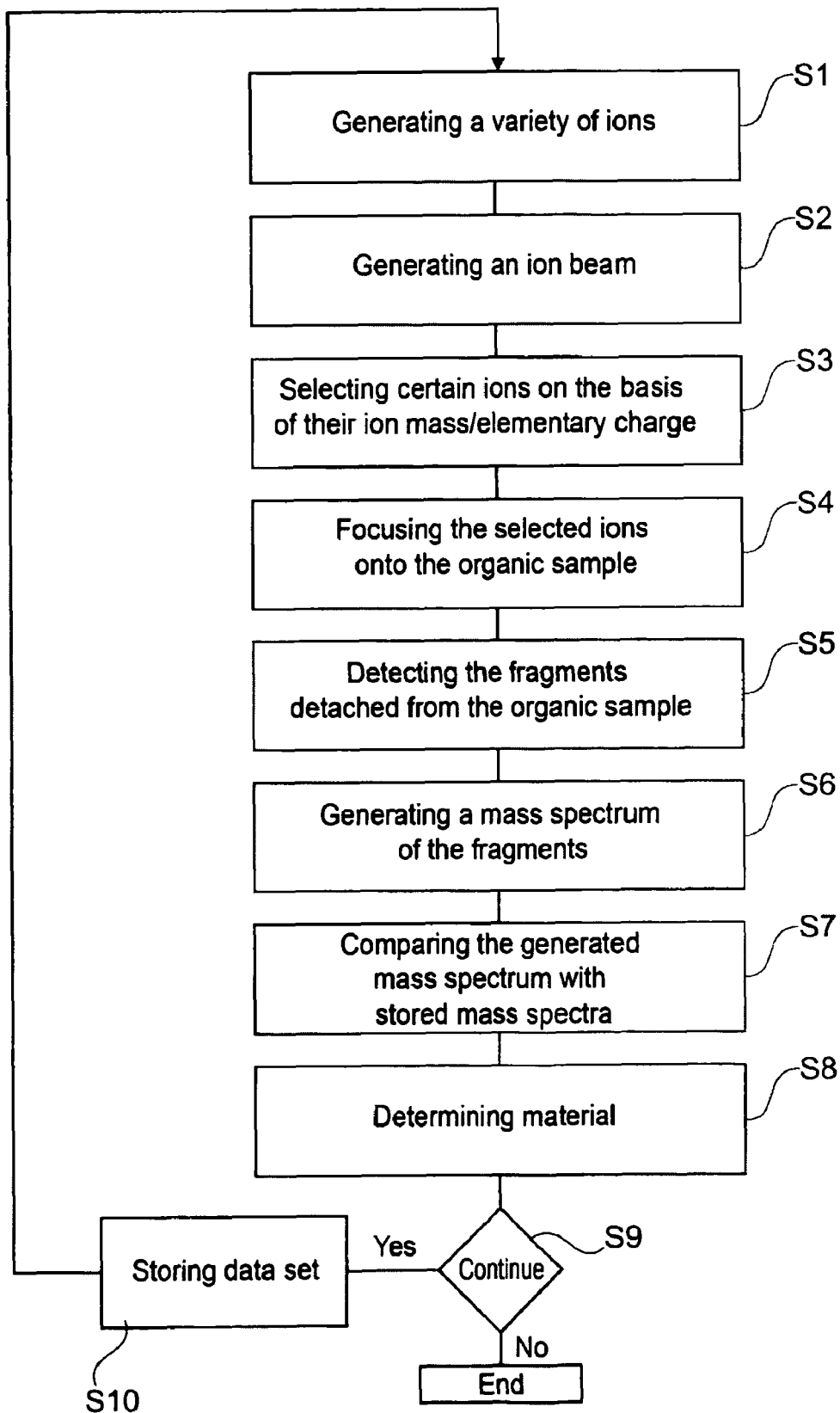
FIG. 2 shows a schematic representation of a sequence of a first embodiment of the method for analyzing an organic sample.

FIG. 2 shows a flow chart of steps of the method which may be carried out using the ion beam device 1 illustrated in FIG. 1. FIG. 2 further illustrates the method outlined above. In a method step S1, the ion source 3 generates a variety of ions of different masses and/or different numbers of elementary charges. The variety of ions may be combined to form an ion beam (method step S2). Subsequently, ions having a certain mass and/or number of elementary charges are selected from the ion beam with the aid of the Wien filter 6 (method step S3). Only the selected ions may be focused onto the organic sample 11 to be analyzed (method step S4). When the ion beam hits the surface of the organic sample 11, fragments are detached from the organic sample 11 and are detected (method step S5). With the aid of the ion mass analyzer 12, all the above-mentioned fragments may be displayed in a mass spectrum with the aid of SIMS (method step S6), this mass spectrum then being compared in a method step S7 with the mass spectra of different materials stored in the memory unit 14 (method step S7). In this way, the material of the fragment, i.e. of the organic sample 11 may be determined (method step S8).

In this embodiment of the method, it is provided that the method may be carried out multiple times consecutively (method step S9). If the method is carried out multiple times consecutively, information is stored in a method step S10 about the location of the organic sample 11 onto which the ion beam was focused, and about the determined material as a data set. In this way, multidimensional information about the organic sample 11 may be compiled. For compiling two-dimensional information, the method may be carried out initially in one plane of the organic sample 11 at least one first location of the organic sample. Information about the first location and the material determined at the first location may be stored as a first data set. Furthermore, the method is carried out at least one second location of the organic sample 11. Information about the second location and the material determined at the second location may be stored as a second data set. For compiling three-dimensional information, the above-described method may be carried out not only with respect to one plane of the organic sample 11, but with respect to multiple planes which are situated one on top of the other or next to one another, for example. For example, for compiling three-dimensional information, it is provided that the organic sample 11 may be cut at well-defined locations using the ion beam, so that recesses are produced. Alternatively, it is provided that a hole is drilled in the organic sample 11 with the aid of the ion beam. The material composition of the organic sample at the recess or hole is than examined with the aid of the method according to the system described herein. Different planes of the organic sample 11 situated substantially perpendicularly to the recess and being gradually exposed using the ion beam may then be examined with the aid of the method according to the system described herein.

Figure 3:
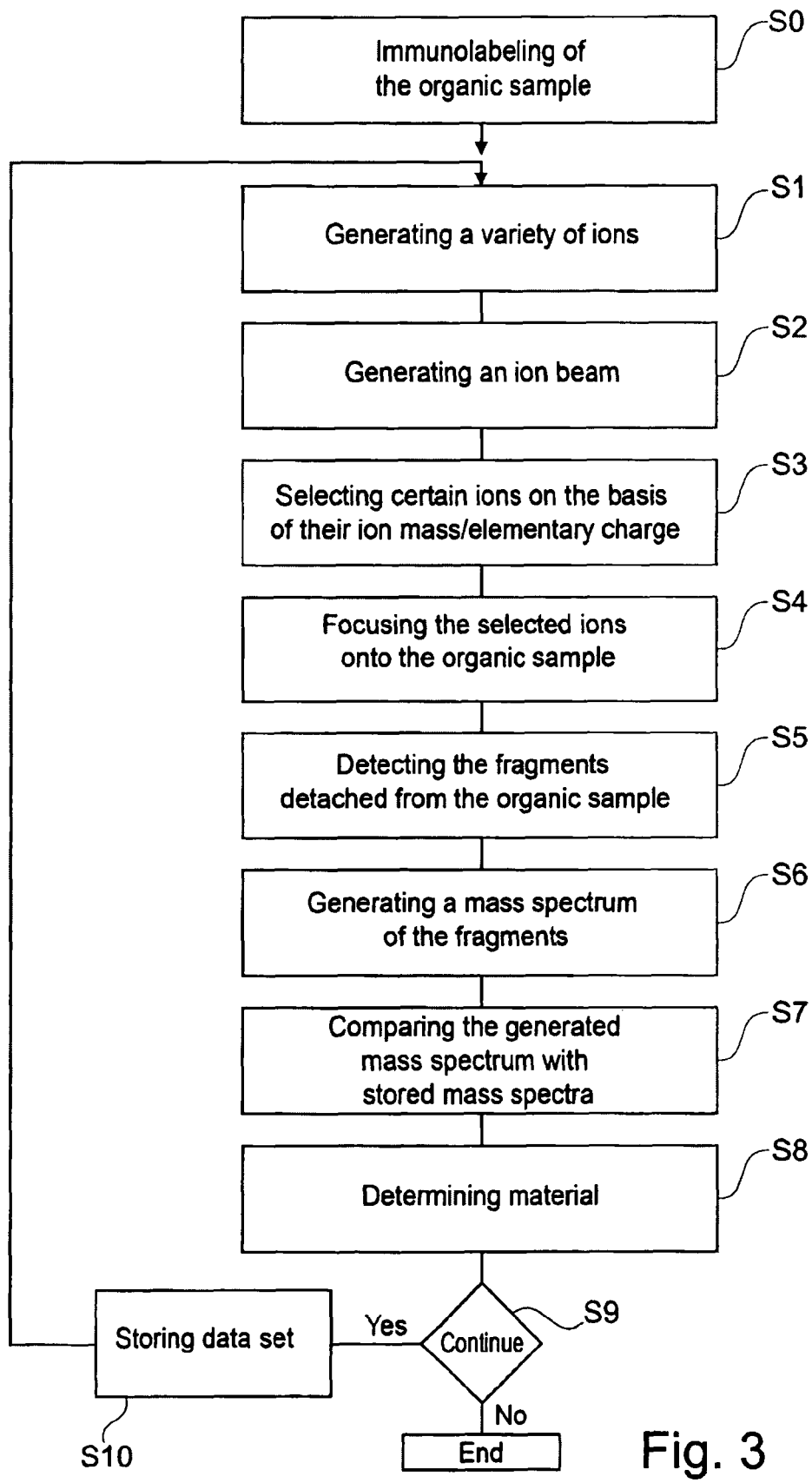
FIG. 3 shows a schematic representation of a sequence of a second embodiment of the method for analyzing an organic sample.

In a further embodiment of the method, which may be carried out with the ion beam device 1 according to FIG. 1 and is discussed in greater detail in FIG. 2, the organic sample 11 may be initially immunolabeled (see FIG. 3). In this case, a specific protein marked using a gold, platinum, or silver cluster may be introduced into the organic sample 11 (method step S0), which was discussed in greater detail above. The specific protein may then be bonded with other proteins of the organic sample 11 on the basis of the "key-lock principle." The method is then carried out, which was discussed in greater detail using FIG. 2. When examining the organic sample 11 with the aid of the method, it is thus possible not only to draw conclusions about the composition of the organic sample 11, but also to draw conclusions about the behavior of the other proteins, for example, their distribution and bonding behavior.

Figure 4:
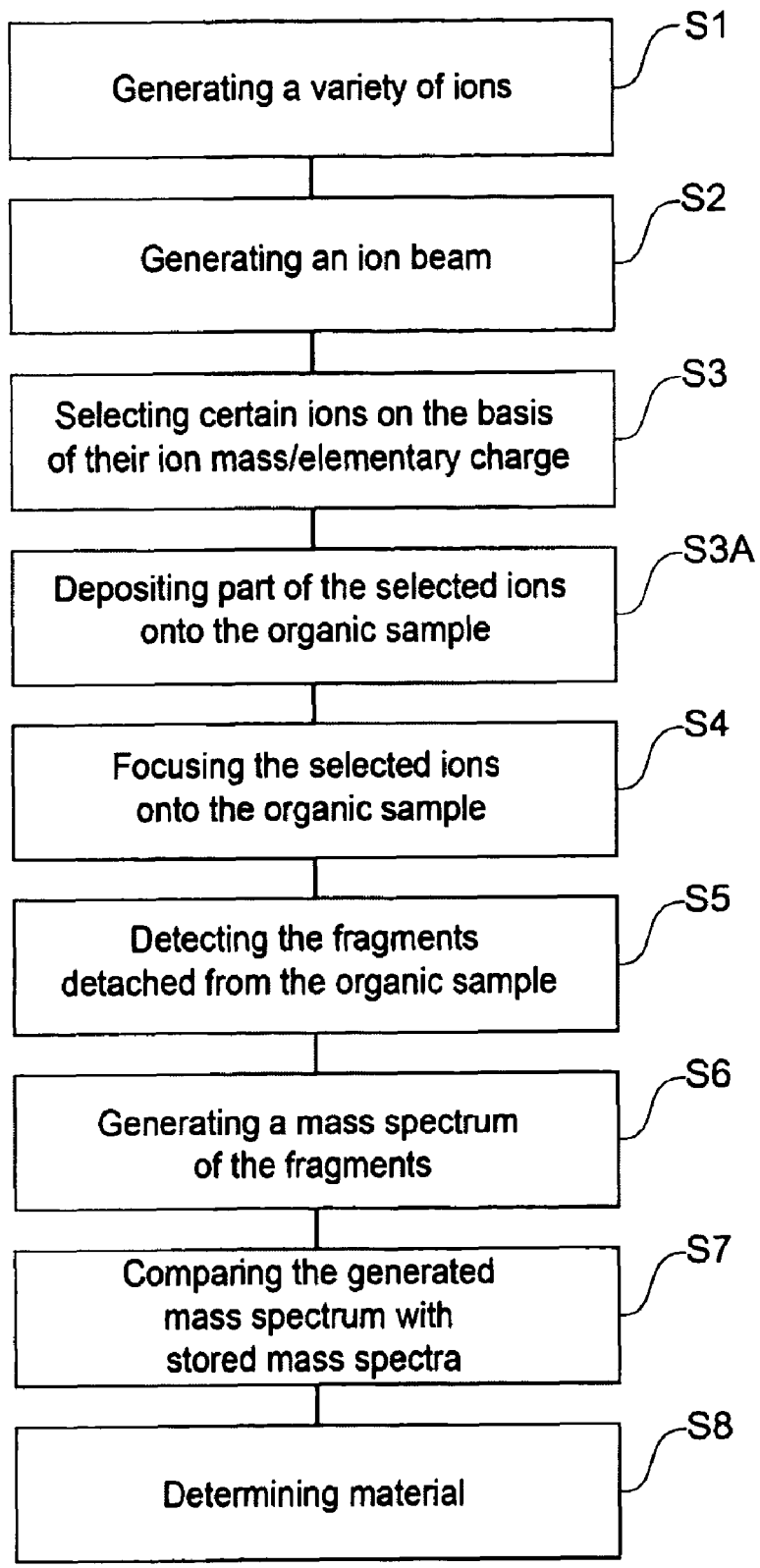
FIG. 4 shows a schematic representation of a sequence of a third embodiment of the method for analyzing an organic sample.

FIG. 4 shows a flow chart of another embodiment of the method. The method of FIG. 4 is based on the method of FIG. 2, so that reference is initially made to the explanations to FIG. 2. In addition, a method step S3A, in which selected ions are continuously deposited on the organic sample 11 or slightly penetrate into the organic sample 11, may be added between method step S3 and method step S4. In particular, in this embodiment, gold or silver ions are provided, which remain in the ion beam as selected ions. Considerations have led to the conclusion that these ions are not only suitable for detaching large fragments of the organic sample 11, but depositing these ions on the organic sample 11 also reduces the work function of the organic sample 11, thus facilitating the detachment of fragments from the organic sample 11.

Figure 5:
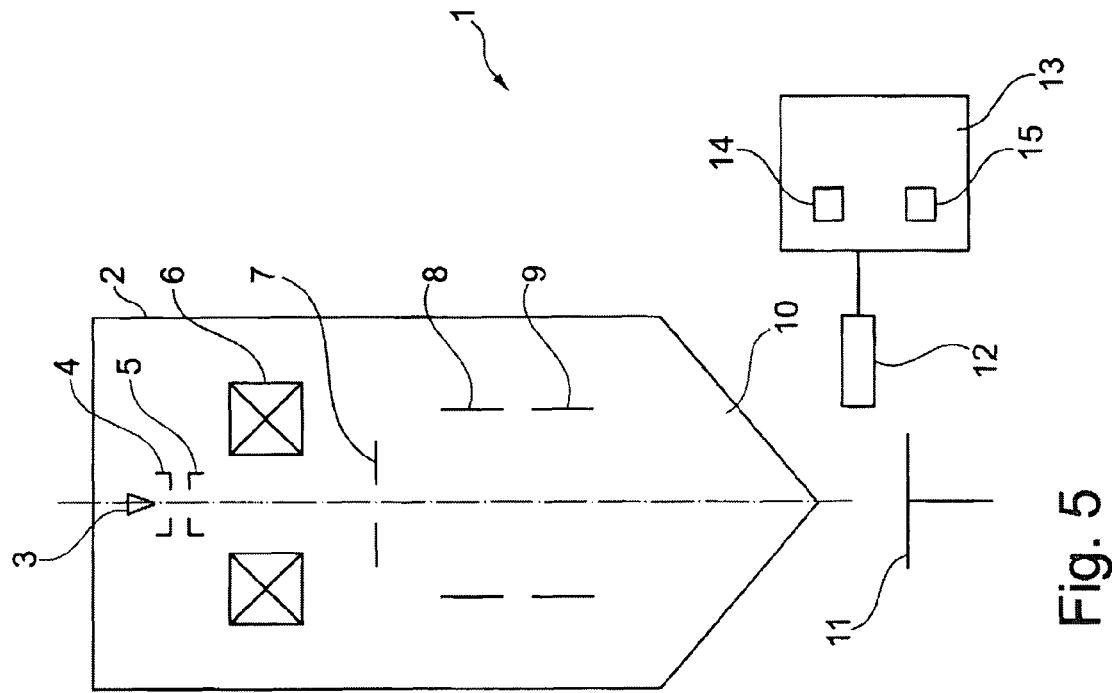
FIG. 5 schematically shows a particle beam device having an ion beam device and an electron beam device according to an embodiment of the system described herein.
Figure 5:
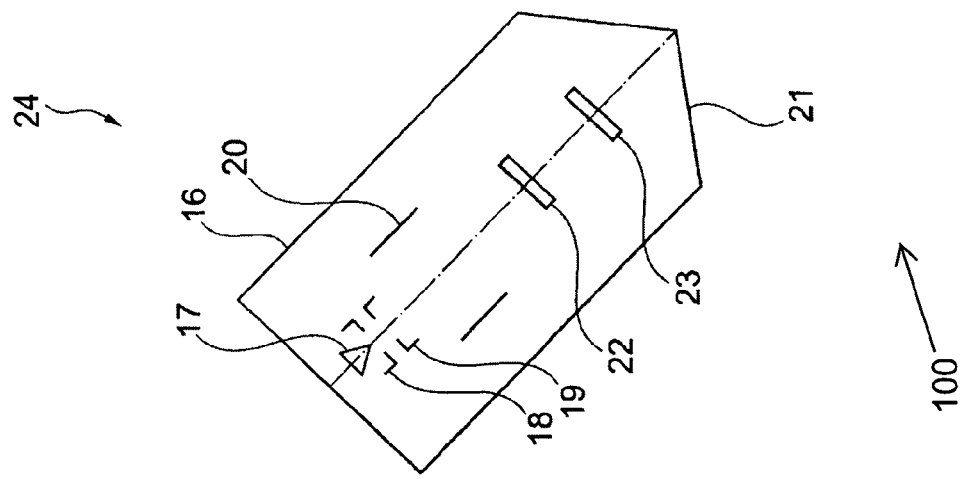

FIG. 5 shows a schematic representation of a particle beam device 100 in which the method according to the system described herein may be used. In addition to the ion beam device 1 described in FIG. 1, the particle beam device 100 according to FIG. 5 may also have an electron beam device 24, which may be used as a scanning electron microscope. The electron beam device 24 may have an electron column 16, in which units of the electron beam device 24 are situated. Thus, an electron source 17 may be provided, which generates electrons which are extracted with the aid of a first electrode 18. The electrons may be accelerated to a predefinable potential with the aid of a second electrode 19. The electrons may then be passed through a condenser lens 20, whereby an electron beam is formed, which, with the aid of an objective lens 21, is focused onto the organic sample 11 to be analyzed. Scanning electrodes (not illustrated) situated on the objective lens 21 ensure that the electron beam may be scanned over the organic sample 11. When the electron beam hits the organic sample 11, interaction particles are formed, in particular secondary electrons and backscattered electrons, which are detected with the aid of a first detector 22 and a second detector 23 and used for imaging. It is thus possible to image the surface of the organic sample 11. It should be pointed out that the detector(s) for the above-mentioned interaction particles may also be situated outside the electron column 16, for example, next to the ion mass analyzer 12. Furthermore, FIG. 5 shows a system in which the ion beam column 2 is vertical, while the electron column 16 is oriented at an angle to the ion beam column 2. The system described herein is, however, not limited to a system of this type. Instead, the ion beam column 2 and the electron column 16 may be situated in any suitable position with respect to each other. For example, the electron column 16 may be vertical, while the ion beam column 2 may be situated at an angle to the electron column 16.

Figure 6:
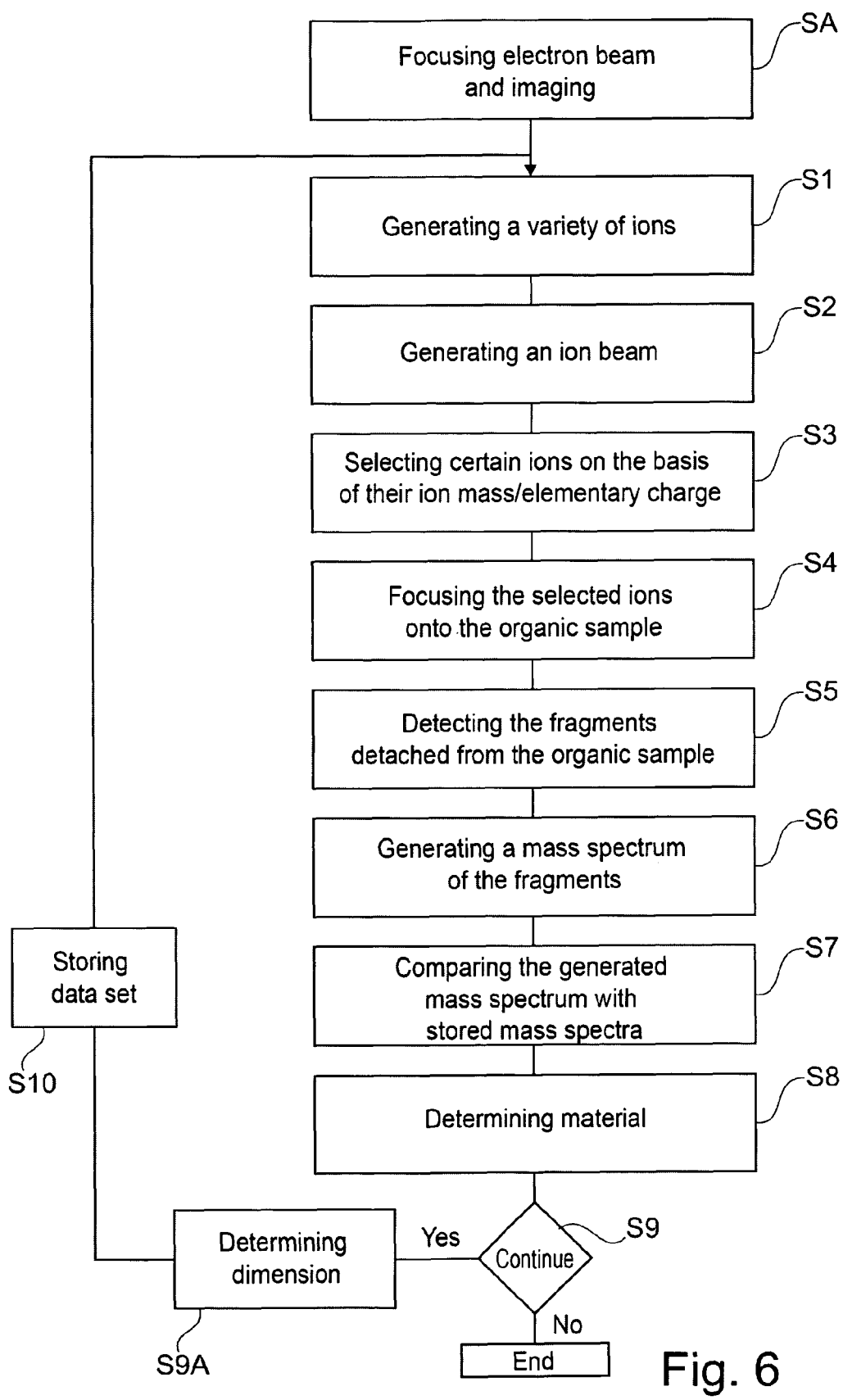
FIG. 6 shows a schematic representation of a sequence of an embodiment of the method for analyzing an organic sample, which is carried out using the particle beam device according to FIG. 5.

The method, illustrated in greater detail in FIG. 6, may be carried out with the help of the particle beam device 100 illustrated in FIG. 5. The method of FIG. 6 is based on the method of FIG. 2, so that reference is initially made to the previous explanations. In addition, in the method according to FIG. 6, the electron beam of the electron column 16 may initially be focused onto the organic sample 11, so that the surface of the organic sample 11 is imaged (method step SA). A zone of the organic sample 11 may then be selected, which is to be examined in greater detail with the aid of the further method.

The following is also provided in this embodiment: to examine the organic sample 11, it is initially cut at well-defined locations in a targeted manner, using the ion beam, so that recesses are formed. The material composition of the organic sample 11 at the recess may then be examined with the aid of the method according to the system described herein. The dimension of the recess (i.e., its depth) should be accurately determined (method step S9A), so that conclusions may be drawn about the distribution of material in the organic sample 11. The corresponding information regarding the location of the organic sample 11 on which the ion beam has been focused, the determined material, and the determined dimension may be stored in the method step S10 as a data set, so that basically a "multidimensional" image of the organic sample 11 may be generated.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method for analyzing an organic sample, comprising:
generating ions having at least one of: a predefinable mass and a predefinable number of elementary charges;
generating at least one ion beam from the ions;
directing the ion beam onto at least one organic sample;
detecting at least one fragment, wherein the fragment is detached from the organic sample using the ion beam, and wherein detecting the at least one fragment includes using an ion mass analyzer to generate a mass spectrum;
comparing the generated mass spectrum with at least one mass spectrum stored in a database; and
determining at least one material of the organic sample based on the comparison between the generated mass spectrum and the stored mass spectrum.

2. The method as recited in claim 1, wherein detecting the at least one fragment further includes detecting multiple fragments, wherein the multiple fragments are detached from the organic sample using the ion beam, and wherein the ion mass analyzer generates the mass spectrum using the multiple fragments.

3. The method as recited in claim 1, wherein multiple mass spectra are stored in the database, each of the multiple mass spectra originating from a different material.

4. The method as recited in claim 1, wherein the ions that are generated include both first ions and second ions, the first ions having at least one of: a first predefinable mass and a first predefinable number of elementary charges, and the second ions having at least one of: a second predefinable mass and a second predefinable number of elementary charges, the second ions being different from the first ions according to at least one of: (i) the second predefinable mass being different from the first predefinable mass and (ii) the second predefinable number of elementary charges being different from the first predefinable number of elementary charges.

5. The method as recited in claim 4, wherein the first ions or the second ions are selected from the generated ion beam and are directed to the organic sample.

6. The method as recited in claim 1, wherein the ions are or contain at least one of the following elements: Si, Cr, Fe, Co, Ni, Ge, In, Sn, Au, Ag, Pb, Bi, Nd, Cs, and As.

7. The method as recited in claim 1, wherein the ions include a type of ions whose mass is greater than that of gallium.

8. The method as recited in claim 1, wherein the ions include ions having a mass greater than 100 atomic mass units.

9. The method as recited in claim 1, wherein the ions are deposited on the organic sample, reducing the work function of the organic sample for detaching the fragment.

10. The method as recited in claim 1, further comprising:
immunolabeling the organic sample to be analyzed.

11. The method as recited in claim 1, wherein the ion beam is focused onto the organic sample.

12. The method as recited in claim 1, wherein the method is carried out at least one first location of the organic sample, and information about the first location and about the material determined at the first location is stored as a first data set, and wherein the method is carried out at least one second location of the organic sample, and information about the second location and about the material determined at the second location is stored as a second data set.

13. The method as recited in claim 1, further comprising:
generating an image of the organic sample using at least one focused electron beam.

14. The method as recited in claim 13, further comprising:
selecting a zone of the organic sample to be examined using the image.

15. The method as recited in claim 13, further comprising:
producing a recess in the organic sample using the ion beam.

16. The method as recited in claim 15, further comprising:
determining at least one dimension of the recess using the image.

17. An ion beam device for analyzing an organic sample, comprising:
at least one ion generator that generates ions which have at least one of: a predefinable mass and a predefinable number of elementary charges;
at least one ion beam generator that generates at least one ion beam from the ions;
at least one ion beam director that directs the ion beam onto at least one organic sample;
at least one detector that detects at least one fragment which is detached from the organic sample using the ion beam, the detector having at least one ion mass analyzer that generates a mass spectrum;
at least one comparing device that compares the generated mass spectrum with at least one mass spectrum stored in a database; and
at least one determining device that determines at least one material of which the organic sample is composed on the basis of the comparison between the generated mass spectrum and the stored mass spectrum.

18. The ion beam device as recited in claim 17, further comprising:
an electron beam generator that generates an electron beam.

19. The ion beam device as recited in claim 18, further comprising:
an electron beam director that directs the electron beam onto the organic sample.

* * * * *